United States Patent [19]

Takita et al.

[11] 4,369,253

[45] Jan. 18, 1983

[54] GROWTH PROMOTING METHOD FOR BASIDIOMYCETES

[75] Inventors: Hitoshi Takita, Tokyo; Toshihiko Wada, Mibu; Yutaka Mukaida, Tokyo; Satoru Enomoto, Fujisawa; Akiyoshi Nakajima, Mibu; Azuma Okubo, Mibu, all of Japan

[73] Assignee: Kureha Kagaku Kogyo Kabushiki Kaisha, Tokyo, Japan

[21] Appl. No.: 247,218

[22] Filed: Mar. 24, 1981

Related U.S. Application Data

[63] Continuation-in-part of Ser. No. 76,666, Sep. 18, 1979, abandoned.

[30] Foreign Application Priority Data

Jun. 11, 1979 [JP] Japan .................................. 54/73361
Dec. 24, 1980 [JP] Japan ................................ 55/165723

[51] Int. Cl.³ .......................... C12N 1/38; C12N 1/14
[52] U.S. Cl. ..................................... 435/244; 435/254
[58] Field of Search .......................................... 435/244

[56] References Cited

U.S. PATENT DOCUMENTS 3,183,171  5/1965  Schreiner ........................... 435/244
3,873,424  3/1975  Kimura et al. ..................... 435/244
4,162,939  7/1979  Yoshikumi et al. ................. 435/254

OTHER PUBLICATIONS

Turner, Fungal Metabolites, Academic Press, pp. 14-16, (1971).
The Merk Index, 9th Ed., p. 877, (1976).

*Primary Examiner*—Alvin E. Tanenholtz
*Attorney, Agent, or Firm*—Wegner & Bretschneider

[57] ABSTRACT

Disclosed is a method for producing the high-quality mycelia of the Basidiomycetes from culture thereof by promoting growth of the fungus as well as differentiation of the cells and attendant organization thereof by adding to the culture medium a straight chain saturated aliphatic alcohol with a catbon number within a specified range of 26 to 36 carbon atoms.

2 Claims, No Drawings

GROWTH PROMOTING METHOD FOR BASIDIOMYCETES

CROSS-REFERENCE TO RELATED APPLICATION

The present application is a continuation-in-part of application Ser. No. 76,666, filed Sept. 18, 1979 and entitled "GROWTH PROMOTING METHOD FOR BASIDIOMYCETES" (now abandoned).

BACKGROUND OF THE INVENTION

This invention relates to a method for promoting growth of the fungi of Basidiomycetes by means of cultivation.

More particularly, this invention relates to a normal aliphatic alcohol represented by the formula: $C_nH_{2n+1}OH$, wherein n is an integer of 26 to 36, is very effective in promoting the growth of a fungus belonging to Basidiomycetes when the alcohol is added to the conventional culture media of the fungus.

Increasing interest is shown recently in use of the fungi of Basidiomycetes as the base material for medicines and health foods, but low rate of growth of such fungi in cultivation thereof as compared with other microorganisms such as bacteria or yeast is causing a bottleneck for inductrial utilization of these fungi.

Addition of nutrients such as inorganic salts, extracts from natural products, etc., in the medium has been proposed as a measure for promoting growth of the basidiomycetes in cultivation thereof. Addition of such nutrients in the culture medium has indeed an effect of promoting cell division of the basidiomycetes, but it can not bring about a similar effect for differentiation of the cells and attendant organization thereof, and hence no desired promotion of growth and propagation is provided. Thus, such measure is unable to realize production of high-quality mycelia of the above-mentioned fungi at a high rate.

We found that growth of the basidiomycetes is markedly promoted and also differentiation and organization of the cells are advanced by adding in the culture medium a small quantity of a straight chain saturated aliphatic alcohol with a carbon number within a specified range, thereby allowing obtaining of high-quality mycelia of the fungi.

The object of this invention, therefore, is to provide a method capable of promoting growth and propagation of the basidiomycetes and producing the high-quality mycelia of the fungi by means of cultivation thereof.

The invention is described in detail hereinbelow.

DETAILED DESCRIPTION OF THE INVENTION

The straight chain saturated aliphatic alcohol added in the medium for cultivation of the basidiomycetes according to this invention is represented by the following general formula:

$$C_nH_{2n+1}OH \quad (I)$$

wherein n is an integer of 26 to 36. Examples of such straight chain saturated aliphatic alcohol include the following: n-hexacosanol-1, n-heptacosanol-1,n-octacosanol-1, n-nonacosanol-1, n-triacontanol-1, n-hentriacontanol-1, n-dotriacontanol-1, n-tritriacontanol-1, n-tetratriacontanol-1, n-pentatriacontanol-1, and n-hexatriacontanol-1. Most preferred among these alcohols for the purpose of this invention are those having a carbon number of 28 to 32.

It is very interesting to note the fact that, among these alcohols, those having an odd carbon number exist rarely in the natural products but have a growth and propagation promoting action for the basidiomycetes. Most of the long-chain aliphatic alcohols existing in plants, such as n-hexacosanol-1, n-octacosanol-1, n-triacontanol-1, etc., are even in their carbon number, and it is reported (Science, Vol. 195, 1339 (1977) and Plant Physiol. Vol. 61, 855 (1978)) that, among these long-chain alcohols, n-triacontanol-1 alone has a specific effect of promoting growth of higher plants, but there is available no report on growth activity for the micro-organisms.

Thus, among long-chain alcohols, n-triacontanol-1 alone has a specific action for promoting growth of higher plants, while all of the long-chain alcohols with a carbon number of 26 to 36 used in this invention have the activities for promoting growth of the basidiomycetes as well as differentiation of the cells and attendant organization thereof.

The long-chain alcohols represented by the above-shown general formula (I) can produce the above-stated growth promoting effect for the basidiomycetes by merely adding a small quantity of said alcohol, or within the range of 0.01 to 10 ppm, in the medium. From the viewpoints of economy and solubility of long-chain alcohol in water, it is advisable to add such alcohol in an amount of 0.05 to 10 ppm in the medium. It is also possible to use a mixture of two or more of the long-chain alcohols.

Although the long-chain alcohols used in this invention can be chemically synthesized, some of them can be also easily obtained from natural sources through extraction either singly or in the form of a mixture.

As for the culture medium in which the long-chain alcohol is to be added, there may be used a wide variety of media which are generally employed for cultivation of the basidiomycetes. For instance, there may be used the media containing carbon sources such as starch, sucrose, maltose, dextrose, wood chips, etc., nitrogen sources such as rice bran, wheat bran, corn steep liquor, peptone, broth, meat extract, soybean flour, powdered cottonseed, yeast extract, malt extract, urea, nitrates, etc., inorganic salts such as calcium salt, magnesium salt, sodium salt, zinc salt, copper salt, iron salt, manganese salt, etc., and other nutrients such as vitamins.

The culture medium may be either solid or liquid, and stationary or submerged culture may be employed in this invention. Addition of the long-chain alcohol into the medium may be made either before start of the cultivation or in the course of the cultivation after the fungus has grown to a certain degree.

The Basidiomycetes for which this invention is applicable include a wide variety of fungi that taxologically belong to the "Basidiomycota", but most preferred for use in this invention are the fungi belonging to the order Agaricales or Aphyllophorales of Homobasidiae, such as for example *Armillariella mellea* (Fr.) Karst, *Tricholoma matsutake* (S. Ito et Imai) Sing., *Lentinus edodes,* (Berk.) Sing., *Coriolus versicolor* (Fr.) Quèl., *Grifola gigantea* (Fr.) Pilàt, *Favolus Arcularius* (Fr.) Ames, etc. The taxological nomenclature of the basidiomycetes is based on "Coloured Illustrations of Fungi of Japan" by ROKUYA IMAZEKI and TSUGUO HONGO.

The outstanding effect of this invention is not limited to promoted growth of the mycelia of the basidiomycetes; it also allows obtaining of mycelia with small bulk specific gravity and advanced organization in cultivation of for instance Coriolus versicolor (Fr.) Quél. Further, there are obtained clusters of mycelia in cultivation of Armillaria Mellea (Fr.) Karst, and the mycelia obtained in cultivation of Laetiporus sulphureus (Fr.) Bond. et Sing. present reddish orange which is closely analogous to the color of natural fruit bodies. When Laetiporus sulphureus is cultivated according to the conventional method, there are obtained light orange colored mycelia.

The histological change of the mycelia in cultivation of the basidiomycetes according to this invention appears to be based upon with the fact that the long-chain saturated aliphatic alcohol added in the culture medium is greatly concerned with growth and propagation of the fungi, in view of the change of phenol oxidase activity, in cultured broth.

The invention is now described in further detail by way of the following examples, but it is to be understood that the scope of this invention is not limited to these examples.

EXAMPLE 1

Each of 20 ml ethanol solutions dissolved therein 6 mg portions of straight chain saturated alcohols with different carbon numbers varying within the range of 26 to 36 was added dropwise into 2 liters of water respectively, and after dissolving, ethanol was evaporated to prepare the aqueous solutions of the alcohols with 3 mg/l concentration each.

The rational formulae and melting points of the straight chain saturated aliphatic alcohols used in this example are shown in Table 1 below.

TABLE 1

| Straight chain saturated aliphatic alcohol | Rational formula | M.p. (°C.) |
|---|---|---|
| n-hexacosanol-1 | $C_{26}H_{53}OH$ | 78–80 |
| n-octacosanol-1 | $C_{28}H_{57}OH$ | 81–83 |
| n-nonacosanol-1 | $C_{29}H_{59}OH$ | 82–84 |
| n-triacontanol-1 | $C_{30}H_{61}OH$ | 85–87 |
| n-hentriacontanol-1 | $C_{31}H_{63}OH$ | 86–88 |
| n-dotriacontanol-1 | $C_{32}H_{65}OH$ | 87–89 |
| n-tetratriacontanol-1 | $C_{34}H_{69}OH$ | 90–91 |

TABLE 1-continued

| Straight chain saturated aliphatic alcohol | Rational formula | M.p. (°C.) |
|---|---|---|
| n-hexatriacontanol-1 | $C_{36}H_{73}OH$ | 91–92 |

In the thus prepared long-chain alcohol solutions (2 liters each) were dissolved 120 g of glucose, 15 g of yeast extract and 4 g of malt extract to obtain liquid culture media.

Seventy-five ml each of the obtained media was pipetted into 15 Erlenmeyer flasks (200 ml capacity), and after cotton-plugged, each flask was sterilized at 120° C. for 15 minutes. The medium in each of the Erlenmeyer flasks was inoculated with 0.8 mg of the beforehand prepared seed culture of Coriolus versicolor (Fr.) Quél. (FERM-P No. 2,413) and subjected to stationary culture at 25° C. For the sake of comparison, the cultivation was carried out in a medium of the same composition but not added with long-chain alcohol under the same conditions.

After a given period of cultivation, the produced mycelia in the respective flasks were separated, washed well with water, ethanol and acetone and then dried at 60°–80° C.

The relation between the days of cultivation and the obtained dry culture yield has been observed.

When Coriolus versicolor is cultivated in the media added with straight chain saturated aliphatic alcohols according to this invention, a sharp increase in yield of mycelia is observed after the 14th day from start of the cultivation, indicating a prominent growth and propagation promoting effect of the straight chain alcohols on the basidiomycetes.

EXAMPLE 2

Cultivation carried out by following the same procedure as Example 1 but by using the aqueous solutions of n-triacontanol-1 in concentrations of 3 ppm, 2 ppm, 1 ppm and 0.1 ppm, respectively, as straight chain saturated aliphatic alcohol.

As control, there was similarly performed cultivation in a medium same as said above except that no alcohol was added.

The results of measurements on change of culture elements with time are shown in Table 2 below.

TABLE 2

| Days of culture | | Triacontanol concentration (ppm) | Sugar content in filtrate (%)*1 | Reducing sugar concentration in filtrate (%) | pH | Enzyme activity (u/mg)*2 | Dry culture yield (g/100 ml)*3 | Index*4 |
|---|---|---|---|---|---|---|---|---|
| 8 days | Comparative Example | 0 | 6.0 | 5.97 | 5.00 | 2.09 | 0.559 | 100 |
| | This invention | 0.1 | 6.0 | 5.97 | 5.10 | 0.86 | 0.563 | 101 |
| | | 1 | 6.2 | 6.05 | 5.10 | 0.83 | 0.492 | 88 |
| | | 2 | 6.2 | 5.97 | 5.10 | 0.91 | 0.531 | 95 |
| | | 3 | 5.6 | 5.60 | 5.15 | 0.10 | 0.505 | 90 |
| 14 days | Comparative Example | 0 | 4.6 | 4.57 | 4.32 | 9.69 | 1.451 | 100 |
| | This invention | 0.1 | 4.4 | 4.40 | 4.40 | 8.82 | 1.469 | 101 |
| | | 1 | 4.6 | 4.65 | 4.40 | 7.06 | 1.670 | 115 |
| | | 2 | 4.6 | 4.30 | 4.50 | 8.00 | 1.629 | 112 |
| | | 3 | 4.6 | 4.59 | 4.50 | 6.81 | 1.643 | 113 |
| 21 days | Comparative Example | 0 | 3.5 | 3.36 | 4.40 | 11.10 | 1.944 | 100 |
| | This invention | 0.1 | 2.8 | 2.76 | 4.40 | 10.46 | 2.261 | 116 |
| | | 1 | 3.0 | 2.98 | 4.40 | 10.11 | 2.323 | 120 |
| | | 2 | 3.0 | 3.02 | 4.45 | 7.78 | 2.375 | 122 |

TABLE 2-continued

| Days of culture | Triacontanol concentration (ppm) | Sugar content in filtrate (%)[1] | Reducing sugar concentration in filtrate (%) | pH | Enzyme activity (u/mg)[2] | Dry culture yield (g/100 ml)[3] | Index[4] |
| --- | --- | --- | --- | --- | --- | --- | --- |
| | 3 | 2.7 | 2.56 | 4.40 | 8.52 | 2.671 | 137 |

NOTES:
[1]:Measured by refraction viscometer.
[2]:Phenol oxidase activity in culture filtrate.
[3]:Dry culture yield per 100 ml of medium.
[4]:The dry culture yield from the triacontanol-non-added medium at each sampling date was given as 100.

It is seen from the above table that n-triacontanol-1 rather controls growth of mycelia of *Coriolus versicolor* in the early phase of cultivation, but it comes to show its activity for promoting growth of mycelia visibly from around 14th day of cultivation. It is also noted that the sugar content and reducing sugar concentration in the used medium and filtrate pH are not much different from those of the control, but the phenol oxidase enzyme activity associated with the intracellular factors changes very specifically by presence of n-triacontanol-1 in the medium.

It is to be also noted that the mycelia obtained from cultivation according to this invention were smaller in bulk specific gravity and more solid in tissue than those of the Comparative Examples (control).

EXAMPLE 3

There were prepared the aqueous solutions having dissolved therein n-triacontanol-1 in concentrations of 1 ppm, 3 ppm and 10 ppm, respectively, according to the method described in Example 1, and in each of these solutions (1 liter) were dissolved 60 g of glucose and 7.5 g of yeast extract to form liquid media. For the sake of comparison, there was similarly prepared a medium by dissolving 60 g of glucose and 7.5 g of yeast extract in 1 liter of water but not containing n-triacontanol-1.

One hundred ml each of the thus prepared media including the comparative medium was pippetted into 500 ml Erlenmeyer flasks, and there were prepared 10 incubators for each medium, totalling 40 incubators in all. After sterilization, the medium in each the Erlenmeyer flask was inoculated with 120.8 mg of seed culture of *Coriolus versicolor* (Fr.) Quél. (FERM-P No. 2413) and then subjected to shaking culture at 25° C. After 5-day shaking culture, the produced mycelia from the respective cultures were separated, washed, dried and measured in weight. Also, the phenol oxidase activity of each culture filtrate was determined. The results are shown in Table 3 below.

TABLE 3

| | n-triacontanol-1 loading (ppm) | Dry culture yield[1] (g/100 ml) | Index | Phenol oxidase activity[2] (u/mg) |
| --- | --- | --- | --- | --- |
| This invention | 1 | 0.221 | 119 | 10.74 |
| | 3 | 0.225 | 121 | 10.85 |
| | 10 | 0.218 | 117 | 13.03 |
| Comparative Example (control) | 0 | 0.186 | 100 | 9.95 |

(Notes)
[1]:Dry culture yield per 100 ml of medium.
[2]:Phenol oxidase activity of the culture filtrate.

As apparent from the above results, the prominent effect of this invention was confirmed in shaking culture, too.

EXAMPLE 4

Twenty-five ml of an ethanol solution containing 7.5 mg of n-triacontanol-1 was added dropwise into 2.5 liters of water and n-tiracontanol-1 was perfectly dissolved in water. Then ethanol was evaporated away to obtain the aqueous solutions containing n-triacontanol-1 in concentrations of 1 ppm and 3 ppm, respectively, and in the thus obtained solutions (1 liter each) were dissolved 60 g of glucose, 3 g of yeast extract, 3 g of malt extract and 5 g of peptone to prepare the liquid culture media. Fifty ml each of the thus prepared media was pipetted into ten 200 ml capacity Erlenmeyer flasks, and after cotton-plugged, each of the flasks was sterilized at 120° C. for 15 minutes.

The media in the respective Erlenmeyer flasks were inoculated with 0.8 mg each of seed cultures of *Laetiporus sulphureus* (Fr.) Bond. et Sing. (FERM-P No. 3032), *Armillariella mellea* (Fr.) Karst. (FERM-P No. 982) and *Grifola frondosa* (S. R. Gray) (FERM-P No. 3033) and subjected to stationary culture at 25°±1° C. For the purpose of comparison, there was conducted a similar cultivation operation by using a medium not containing n-triacontanol-1. After a given period of cultivation, the produced mycelia were separated, washed well with water, ethanol and acetone and dried at 60°–80° C. The days of cultivation, dry culture yields and indices as determined for the respective mycelial products are shown in Table 4 below.

TABLE 4

| | | n-triacontanol concentration (ppm) | | | | | |
| --- | --- | --- | --- | --- | --- | --- | --- |
| | | Comparative Example | | This invention | | | |
| | | 0 | | 1 | | 2 | |
| Fungus species | Days of cultivation | Dry culture yield* | Index** | Dry culture yield | Index | Dry culture yield | Index |
| *Laetiporus sulphureus* (Fr.) Bond. et Sing. FERM-P No.3032 | 19 | 0.174 | 100 | 0.240 | 138 | 0.258 | 148 |
| | 29 | 0.278 | 100 | 0.362 | 130 | 0.418 | 150 |

TABLE 4-continued

| | | n-triacontanol concentration (ppm) | | | | | |
|---|---|---|---|---|---|---|---|
| | | Comparative Example | | This invention | | | |
| | | 0 | | 1 | | 2 | |
| Fungus species | Days of cultivation | Dry culture yield* | Index** | Dry culture yield | Index | Dry culture yield | Index |
| Armillariella mellea (Fr.) Karst. FERM-P No.982 | 18 | 1.147 | 100 | 1.377 | 120 | 1.648 | 135 |
| | 28 | 1.445 | 100 | 1.941 | 134 | 2.263 | 157 |
| Grifola frondosa S.F.Gray FERM-P No.3032 | 26 | 0.887 | 100 | 1.034 | 117 | 1.044 | 118 |
| | 32 | 1.514 | 100 | 1.565 | 103 | 1.640 | 108 |

(Notes)
*Dry culture yield (g/100 ml) per 100 ml of medium.
**The dry culture yield from the tricontanol-non-added medium at each sampling date was given at 100.

The above results indicate that n-tiracontanol-1 takes an excellent growth and propagation promoting effect on the above-shown basidiomycetes.

It is to be also noted that the mycelia obtained from the process of this invention are distinguishable in color from those of the comparative examples, that is, in the case of *Laetiporus sulphureus,* the produced mycelia present reddish orange which is closely analogous to the color of the natural fruit bodies, and in the case of *Armillariella mellea,* there is observed more conspicuous formation of mycelial clusters, while in the case of *Grifola frondosa,* the mycelial product has a color close to that of the natural products.

EXAMPLE 5

Preparation of culture medium

Into one liter of distilled water, 20 g of glucose, 2 g of peptone, 1 g of yeast extract, 1 g of $K_2HPO_4$, 0.45 g of $KH_2SO_4$, 0.5 g of $MgSO_4 7H_2O$, 0.12 mg of thiamine hydrochloride and 18 g of agar were dissolved while heating, and the thus prepared solution was divided into 5 portions, and then n-triacontanol-1 of this invention was dissolved into each of the five portions to make the concentration of n-triacontanol-1 in the portions to 0, 1, 5, 10 and 20 microgram/ml, respectively. After sterilizing each portion at 120° C. for 15 min, it was dividedly poured into 5 sterilized dishes in an amount of 20 ml each to be the culture medium.

Fungal inoculation and culture

A fungul body of *Schizophyllum commune* Fr. (FERM-P 1744) previously cultured in pure state was crushed after adding 30 ml of a sterilized aqueous physiological saline solution, and subjected to centrifugation and washing. The thus obtained precipitate of the fungal body was inoculated onto each of the culture medium placed in an aseptic box while using a platinum wire.

The culture of inoculated fungal body was carried out in a thermostat kept at 25° C. for 13 days including first 6 days in the dark and then 7 days under a white light. The size of the colonies of the fungus in each culture medium on 6th day after inoculation was shown in Table 5.

TABLE 5

| | Concentration of n-triacon-tanol-1 (µg/ml) | size (diameter) of Colony in medium, (mm) average of 5 dishes |
|---|---|---|
| Comparative Example | 0 | 25.6 |

TABLE 5-continued

| | Concentration of n-triacon-tanol-1 (µg/ml) | size (diameter) of Colony in medium, (mm) average of 5 dishes |
|---|---|---|
| (control) | (not added) | |
| This invention | 1 | 49.4 |
| | 5 | 45.9 |
| | 10 | 41.3 |
| | 20 | 39.6 |

The average number of fruit bodies formed during 13 days and their average weight were shown in Table 6.

TABLE 6

| | Concentration of n-triacon-tanol-1 (µg/ml) | Number* of fruit body | Raw weight* of fruit body | | Dried weight* of fruit body | |
|---|---|---|---|---|---|---|
| | | | (mg) | Index | (mg) | Index |
| Comparative Example (control) | 0 (not added) | 4.4 | 79 | 100 | 29 | 100 |
| This invention | 1 | 7.5 | 101 | 128 | 37 | 128 |
| | 5 | 9.6 | 149 | 189 | 39 | 134 |
| | 10 | 9.5 | 145 | 184 | 41 | 141 |
| | 20 | 9.8 | 150 | 190 | 53 | 183 |

Note:
*average figures of five dishes of culture.

EXAMPLE 6

Preparation of culture medium

Four parts by volume of sawdust and one part by volume of rice bran were mixed well, and 10 liters of an aqueous solution of n-triacontanol-1 at a predetermined concentration shown in Table 7 was added to 6.6 kg of the mixture, and then the whole mixture was stirred well to be a culture medium.

The culture medium was filled into 105 wide-mouth glass bottles of capacity of 800 ml in an amount of 620 g/bottle, and the bottles were sterilized at 120° C. for 30 min under pressure to prepare the culture medium.

Fungal inoculation and culture

Seed fungus of *Pleurotus ostreatus* (Fr.) Quél. (FERM-P 1746) was inoculated according to a conventional procedure into each bottle containing the culture medium and culture was carried out at 20° to 22° C. By culturing for 30 days, the mycelium proliferated through out the whole medium, particularly in the medium containing n-triacontanol-1. After carrying out an agitation according to a conventional procedure, the culture was continued at 13° to 15° C. for growing the fungal bodies. The yield of the fungus after 41-day culture is shown in Table 7 together with the initial concentration of n-triacontanol-1 in the culture medium.

TABLE 7

|  | Concentration of TC* in the solution (μg/ml) | Concentration of TC in the medium (ppm) | Weight of fruit body (total) (g) | Index of yield of fruit body |
|---|---|---|---|---|
| Comparative Example (control) | 0 (not added) | 0 (not added) | 817 | 100 |
| This invention | 3 | 1.0 | 989 | 121 |
|  | 10 | 2.9 | 1,193 | 146 |
|  | 20 | 6.9 | 1,234 | 151 |
|  | 10** | 2.9 | 1,250 | 153 |

Notes:
*TC means n-triacontanol-1
**Sorbitan monooleate was added to water of the solution at a concentration of 50 micrograms/ml.

EXAMPLE 7

According to the procedures in Example 6, three kinds of culture media were prepared while using normal aliphatic alcohols different in chain length, i.e., n-octacosanol-1, n-nonacosanol-1 and n-triacontanol-1, respectively at a concentration of 10 micrograms/ml in the aqueous solution used in preparing the medium, and the seed fungus of the same fungus used in Example 6 was inoculated to each of the three culture medium. The culture was carried out according to the same procedures as in Example 6 for 40 days to grow the fungus, and then the fruit bodies were collected. The results are shown in Table 8.

TABLE 8

|  | Alcohol in the solution | Concentration of alcohol in the medium (ppm) | Weight of fruit body (g) | Index of yield of fruit body |
|---|---|---|---|---|
| Comparative Example (control) | — | 0 | 762 | 100 |
| This invention | n-octacosanol-1 | 2.9 | 1,135 | 149 |
|  | n-nonacosanol-1 | 2.9 | 1,234 | 162 |
|  | n-triacosanol-1 | 2.9 | 1,166 | 153 |

As is seen in Table 8, the effectiveness of addition of each alcohol is equally conspicuous as compared to the case where no alcohol was added to the culture medium.

EXAMPLE 8

The culture medium was prepared by the procedures of mixing 4.49 kg of sawdust and 2.11 kg of rice bran, adding 10 liters of an aqueous dispersion of 0.1 g of n-triacontanol-1 in 10 liters of water by adding 0.5 g of an emulsifier (Tween 80) to the mixture and stirring the whole mixture well. As the comparative culture medium, the same mixture as above, however, without adding n-triacontanol-1 and the emulsifier was prepared.

The thus prepared culture medium was filled into 21 widemouth polyethylene bottles in each amount of 620 g, and the comparative culture medium was filled into the other 21 bottles of same type. A seed fungus of Flammulina velutipes (Fr.) Sing. (FERM-P 3045) was inoculated into the medium in the 42 (2×21) polyethylene bottles which had been sterilized in advance at 120° C. for 2 hours, and cultured for 25 days at 18° to 20° C. Then, after carrying out an agitation according to a conventional procedure, the culture was continued for 12 days at 10° to 13° C. for growing the fruit bodies of the fungus. The harvested amount (raw weight) on 37th day of the culture was 115 g/bottle containing the culture medium as compared to only 76 g/bottle containing the comparative culture medium containing no n-triacontanol-1.

EXAMPLE 9

A culture medium was prepared by the procedures of at first mixing 8 parts by volume of sawdust and one part by weight of rice bran well to prepare a mixture weighing 12.5 kg, adding 8.8 liters of an aqueous emulsion containing 88 mg of n-triacontanol-1 emulsified by the addition of 440 mg of tween-80 or the same volume of an aqueous emulsion containing 88 mg of n-nonacosanol-1 equally emulsified by adding the same amount of the same emulsifier to the mixture and stirring the whole mixture well. Separately a comparative culture medium was prepared in the same procedures as above, however, without adding any aqueous emulsion, but adding 8.8 liters of water.

The culture medium and the comparative culture medium were respectively filled in 28 polyethylene bags in an amount of 750 g each (each one liter by volume), and the bags containing culture medium were sterilized at 120° C. for 2 hours under pressure.

After cooling the medium, the seed culture of Pholiota nameko (T. Ito) S. Ito et Imai (FERM-P 3052) was inoculated onto the thus prepared culture medium in each polyethylene bag, and the culture was carried out at 23° to 25° C. for 60 days. Then, after cutting the upper portion of the bags, the culture medium therein was stirred well and sprinkled with water, and then the bag was cooled to 15° C., and the culture was carried out at 15° C. for 20 days. The raw weight of the fungal fruit bodies collected from the bags was shown in Table 9.

TABLE 9

|  | Alcohol added | Amount of total (g) | Fruit body per bag (g) | Index of yield of fruit bodies |
|---|---|---|---|---|
| This invention | n-triacontanol-1 | 7,140 | 255 | 176 |
|  | n-nonacosanol-1 | 7,364 | 263 | 180 |
| Comparative Example (control) | — | 4,088 | 146 | 100 |

EXAMPLE 10

An aqueous solution containing 3 ppm of n-triacontanol-1 was at first prepared by dropping 25 ml of ethanol solution wherein 7.5 mg of n-triacontanol-1 was dissolved into 2.5 liters of water and evaporating ethanol from the thus obtained solution. To one liter of the thus prepared solution, 60 g of glucose, 7.5 g of yeast extract, and 2 g of malt extract were dissolved to prepare the culture medium.

Into each of 10 conical flasks of capacity of 200 ml, 50 ml of the culture medium mentioned above was introduced, and after sterilizing at 120° C. for 15 min under a cotton stopper, each 0.8 mg of previously cultured seed cultures of Agaricus campestris Fr. (FERM-P 1748), *Coprinus atramentarius* (Fr.) Fr. (FERM-P 1750), *Boletus edulis* Fr. (FERM-P 1754) and *Sullus luteus* (Fr.) S. F. Gray (FERM-P 5829) was inoculated and cultured at 25°±2° C. keeping to stand still. After culturing for a predetermined period of time, the grown mycelia of each flask was separated, washed with water, ethanol and acetone in this order and dried at 60° to 80° C. The dry weight of the fungal bodies its index and the days of culture were shown in Table 10. The same cultural results obtained by inoculating each of the same species of fungus into the same culture medium, however, lacking the alcohol and culturing under the same conditions and the same period of time were also shown in Table 10 for comparison.

TABLE 10

| Fungal Species | Period of culture (days) | Concentration* of alcohol (mg/l) | pH of culture medium | Concentration of reducing sugar (5) | Yield of fungal bodies (g/l) | Index of fungal bodies |
| --- | --- | --- | --- | --- | --- | --- |
| Agaricus | 81 | 3 | 5.84 | 4.00 | 5.63 | 127 |
| campestris | 81 | 0 | 6.80 | 4.85 | 4.43 | 100 |
| Coprinus | 42 | 3 | 4.90 | 3.00 | 6.83 | 122 |
| atramentarius | 42 | 0 | 5.08 | 3.55 | 5.61 | 100 |
| Boletus | 21 | 3 | 5.52 | 0.90 | 22.5 | 134 |
| edulis | 21 | 0 | 5.35 | 1.35 | 16.8 | 100 |
| Suillus | 36 | 3 | 6.10 | 0.25 | 36.7 | 123 |
| luteus | 36 | 0 | 5.72 | 0.61 | 29.8 | 100 |

Note:
*Alcohol is n-triacontanol-1.

As is seen in Table 10, n-triacontanol-1 acted as a growth-promoting agent of each fungal species.

EXAMPLE 11

Into six sets of the standard culture medium prepared by dissolving 6 parts by weight of glucose, 0.75 part by weight of yeast extract and 2 parts by weight of malt extract into 100 parts by weight of water, 4 ppm of triacontanol, 100 and 500 ppm of a commercial vegetable juice and 100 and 500 ppm of a commercial tomato juice were respectively added, the concentration of the juices being determined on dry matter in the respective juices.

The thus prepared 6 kinds of culture medium were respectively sterilzed in 6 conical flasks at 120° C. for 15 min, and each 0.8 mg of the beforehand seed-culture of *Coriolus versicolor* (Fr.) Quél. was inoculated to each of 6 conical flasks, and the flasks were subjected to culture at 25° C. One of the 6 culture medium without addition of triacontanol or vegetable juice was used as control for comparison.

After 14 days of stational cultivation, the thus produced mycelia in each flask were collected by filtration, washed well with water, ethanol and acetone in this order, and then dried at 60° to 80° C. to be weighed. The results of weighing are shown in Table 11.

TABLE 11

| | | Dried mycelial yields | |
| --- | --- | --- | --- |
| | Additive in medium | Dry weight of mycelia (g) | Index |
| This invention | 4 ppm of triacontanol | 3.663 | 124 |
| Comparative | | | |
| Examples | | | |
| 1 | 0 (control) | 2.954 | 100 |
| 2 | 100 ppm of tomato juice | 3.043 | 103 |
| 3 | 500 ppm of tomato juice | 3.002 | 102 |
| 4 | 100 ppm of vegetable juice | 3.102 | 105 |
| 5 | 500 ppm of vegetable juice | 2.751 | 93 |

As is seen in Table 11, the effectiveness of vegetable- or tomato juice in accelerating the growth of the fungus (that is, the increasing the dry weight of mycelia) could not be recognized as compared to the effectiveness of triacontanol.

What is claimed is:

1. A method of cultivating a fungus of Basidiomycetes wherein said fungus is cultivated in a medium to which at least one of the straight-chain saturated aliphatic alcohols represented by the formula $C_nH_{2n+1}OH$, wherein n is an integer of 26 to 36, has been added to produce a concentration of 0.05 to 10 ppm of said alcohol.

2. The method of claim 1, wherein n is 28 to 32.

* * * * *